United States Patent [19]

Elger et al.

[11] 4,124,708
[45] * Nov. 7, 1978

[54] NOVEL AGENTS AND NOVEL METHODS FOR INDUCING ABORTIONS

[75] Inventors: Walter Elger; Karl Petzoldt, both of Berlin, Fed. Rep. of Germany

[73] Assignee: Schering, A.G., Fed. Rep. of Germany

[*] Notice: The portion of the term of this patent subsequent to Jun. 14, 1994, has been disclaimed.

[21] Appl. No.: 781,275

[22] Filed: Mar. 25, 1977

[30] Foreign Application Priority Data

Mar. 31, 1976 [DE] Fed. Rep. of Germany ....... 2614340

[51] Int. Cl.² .............................................. A61K 31/56
[52] U.S. Cl. .................................................. 424/243
[58] Field of Search ......................................... 424/243

[56] References Cited

U.S. PATENT DOCUMENTS 4,029,779  6/1977  Petzoldt et al. ...................... 424/243

Primary Examiner—Elbert L. Roberts
Attorney, Agent, or Firm—Millen & White

[57] ABSTRACT

Novel agents and methods for triggering abortions employ a compound of the formula

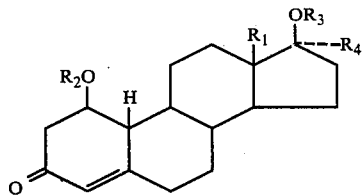

wherein $R_1$ is methyl or ethyl, $R_2$ and $R_3$ are hydrogen or alkanoyl of 1–8 carbon atoms, and $R_4$ is hydrogen or ethynyl.

12 Claims, No Drawings

NOVEL AGENTS AND NOVEL METHODS FOR INDUCING ABORTIONS

BACKGROUND OF THE INVENTION

This invention relates to compositions for and methods of inducing abortion.

SUMMARY OF THE INVENTION

In a compositional aspect, this invention relates to a pharmaceutical composition for inducing abortion in a pregnant human female comprising, in unit dosage form and in admixture with a pharmaceutically acceptable carrier, an active compound of Formula I

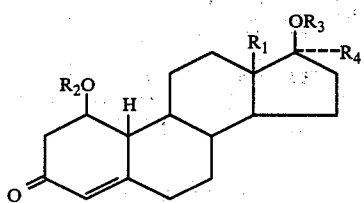

wherein $R_1$ is methyl or ethyl, $R_2$ and $R_3$ are hydrogen or alkanoyl of 1–8 carbon atoms, and $R_4$ is hydrogen or ethynyl.

In a method of use aspect, this invention relates to a method of inducing abortion in a pregnant female comprising administering to the female patient an amount of a composition described above effective to induce an abortion.

DETAILED DESCRIPTION

Alkanoyl $R_2$ and $R_3$ can be identical and, if $OR_3$ is a tertiary hydroxy group, can be different; or $R_2$ can be alkanoyl and $R_3$ hydrogen. Examples of $R_2$ and $R_3$ alkanoyl are: formyl, acetyl, propionyl, butyryl, pentanoyl, hexanoyl, heptanoyl, and octanoyl. Acetyl is preferred.

Compounds of Formula I therefore include those wherein:
(a) $R_1$ is methyl;
(b) $R_1$ is ethyl;
(c) $R_2$ is H, including each of (a)–(b);
(d) $R_2$ is alkanoyl of 1–8 carbon atoms, including each of (a)–(b);
(e) $R_3$ is H, including each of (a)–(d);
(f) $R_3$ is alkanoyl of 1–8 carbon atoms, including each of (a)–(d);
(g) $R_4$ is H, including each of (a)–(f);
(h) $R_4$ is ethynyl, including each of (a)–(f); and
(i) $R_4$ is ethynyl and $R_2$ and $R_3$ are the same.

Peferred compounds of Formula I are:
1$\beta$-acetoxy-19-nortestosterone acetate
1$\beta$-hydroxy-19-nortestosterone
1$\beta$-acetoxynorgestrel
1$\beta$-hydroxynorgestrel
1$\beta$-heptanoyloxynorgestrel
1$\beta$-hydroxynorethisterone
1$\beta$-acetoxynorethisterone.

Many of the compounds of Formula I are known. 1$\beta$-Hydroxy-19-nortestosterone and 1$\beta$-acetoxy-19-noretestosterone acetate have been disclosed in "Recueil" 84 (1965): 626–632 and 1$\beta$-hydroxy- and 1$\beta$-acetoxy-D-norgestrel and -norethisterone described in "Experientia" 30 (1974): 328–329. However, little is known about pharmacological activity of these compounds. "Experientia" sets forth that 1$\beta$-hydroxynorthisterone displays estrogenic activity while 1$\beta$-hydroxynorgestrel exhibits no estrogenic activity.

Esters of Formula I, which have not been described heretofore, e.g., 1$\beta$-heptanoyloxynorgestrel (melting point 149°–150° C. from acetone/diisopropylether), can be obtained by esterifying the corresponding hydroxy compounds. Esterification is accomplished by methods customarily employed in steroid chemistry for the esterification of secondary and tertiary hydroxy groups.

An example of a suitable esterification method is reaction of a steroid with an acid anhydride or acid chloride in the presence of an alkaline catalyst, such as sodium bicarbonate, potassium bicarbonate, potassium carbonate, sodium hydroxide, potassium hydroxide, pyridine, lutidine, collidine, or 4-dimethylaminopyridine. The esterification of secondary hydroxy groups is terminated after about 10–20 hours at room temperature. For partial esterification of a 1-hydroxy group in the presence of a tertiary 17-hydroxy group the esterifying agent is advantageously added at temperatures around 0° C., and the mixture is heated to room temperature only after several hours have elapsed.

Secondary and tertiary hydroxy groups are esterified by treatment with to the esterifying agent for several days at room temperature.

Compunds of Formula I oxygenated in the 1-position have been found to differ clearly from the non-oxygenated starting materials with respect to their pharmacological properties. As compared to non-oxygenated starting materials, compounds of Formula I have increased estrogenic activity, nidation-inhibiting activity in rats and the effect of detachment of uterus epithelium in adult rabbits.

When gravid Rhesus monkeys weighing about 3 kg. are administered a daily subcutaneous dosage of 15 mg. of 1$\beta$-acetoxy-19-nortestosterone acetate or 1$\beta$-acetoxy-norgestrel in 0.8 ml of benzyl benzoate/castor oil 1 : 10, around the 20th to 25th day of gravidity, indications of abortion, i.e., increased uterine bleeding, become visible after approximately 3 days. The treatment is normally continued for another 1 or 2 days so that the active agent is administered for a total of about 3–5 successive days. After termination of the treatment, the abortion can be confirmed by palpation and a hormonal pregnancy test (MCG).

Based on their uterus-epithelium-detaching and abortive activities, which have not been described heretofore, compounds of Formula I can be utilized for triggering abortions by one oral administration or one intramuscular injection. If it is necessary the treatment can be continued for further 1 to 4 days.

The daily dosage for inducing abortion in pregnant females, e.g., humans, is about 0.05–25 mg. of active agent per kg. of body weight, preferably 0.1–5 mg. of active agent per kg. of body weight. The active agents are to be administered as early as possible, preferably within the first 6 weeks of gravidity, to effect triggering of menstruation.

The active agents are processed together with the additives, carriers and/or flavor-ameliorating agents customary in galenic pharmacy into the usual forms of application by conventional methods. Conventional excipients which can be used are pharmaceutically acceptable organic or inorganic carrier substances suitable for parenteral or enteral application and which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglyerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

For oral administration, which is preferred, tablets, dragees, capsules dissolving in the small intestine, suspensions, or solutions are especially suitable About 1–500 mg., preferably 1–100 mg. of active agent is used per dosage unit.

Suitable for parenteral application are oil solutions containing about 10–300 mg. of active agent per 1 ml. of solution, preferably 20–200 mg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Composition of a Dragee:

| | |
|---|---|
| 20.0 mg. | 1β-Hydroxynorethisterone (1β-hydroxy-17α-ethynyl-19-nor-Δ⁴-androsten-17β-ol-3-one) |
| 26.4 mg. | Lactose |
| 26.8 mg. | Corn starch |
| 3.0 mg. | Polyvinylpyrrolidone 25 |
| 3.7 mg. | Talc |
| 0.1 mg. | Magnesium stearate |
| 80.0 mg. | Total weight, brought to about 140 mg. with the usual sugar mixture. |

EXAMPLE 2

| | |
|---|---|
| 25.0 mg. | 1β-Acetoxynorgestrel (1β-acetoxy-17α ethynyl-18-methyl-19-nor-Δ⁴-androsten-17β-ol-3-one) |
| 21.4 mg. | Lactose |
| 26.8 mg. | Corn starch |
| 3.0 mg. | Polyvinylpyrrolidone 25 |
| 3.7 mg. | Talc |
| 0.1 mg. | Magnesium stearate |
| 80.0 mg. | Total weight, brought to about 140 mg. with the usual sugar mixture. |

EXAMPLE 3

Capsule:
100 mg. of finely ground 1β-acetoxy-19-nortestosterone acetate and
100 mg. lactose The ingredients are mixed homogeneously, dispensed into hard gelatin capsules, and encased by a lacquer resistant to gastric acid.

EXAMPLE 4

| Dragee: | |
|---|---|
| 5.0 mg. | 1β-acetoxy-19-nortestosterone acetate |
| 31.4 mg. | Lactose |
| 36.8 mg. | Corn starch |
| 3.0 mg. | Polyvinylpyrrolidone 25 |
| 3.7 mg. | Talc |
| 0.1 mg. | Magnesium stearate |
| 80.0 mg | Total weight, brought to about 140 mg. with the usual sugar mixture. |

EXAMPLE 5

Oily Solution for Intramuscular Injection:

The injection solution is prepared according to customary methods under sterile conditions from the following components:

5000 mg. of 1β-acetoxy-19-nortestosterone acetate is dissolved in a mixture of castor oil/benzyl benzoate (6:4) so that a volume of 100 ml. is obtained. The solution is charged in 1 ml. portions into ampoules, each of which contains 50 mg. of active agent.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make changes and modifications of the invention to adapt it to various usages and conditions.

What is claimed is:

1. A pharmaceutical composition comprising, in admixture with a pharmaceutically acceptable carrier, an amount per unit dosage effective to induce abortion in a pregnant female of a 1β-oxy compound of the formula

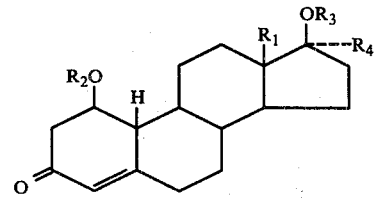

wherein $R_1$ is methyl or ethyl, $R_2$ and $R_3$ are hydrogen or alkanoyl of 1–8 carbon atoms, and $R_4$ is hydrogen or ethynyl.

2. The composition of claim 1, wherein the active compound is 1β-acetoxynorgestrel (1β-acetoxy-17α-ethynyl-18-methyl-19-nor-Δ⁴-androsten-17β-ol-3-one).

3. The composition of claim 1, wherein the active compound is 1β-hydroxynorethisterone.

4. The composition of claim 1, wherein the active compound is 1β-acetoxy-19-nortestosterone acetate.

5. The composition of claim 1, containing the active compound in an amount of 1–500 mg. per dosage unit.

6. The composition of claim 1, containing the active compound in an amount of 1–100 mg. per dosage unit.

7. The composition of claim 1, adapted for administration in the form of a tablet, dragee or capsule.

8. A method of inducing abortion in a pregnant human femal comprising administering to the female patient an amount of a composition of claim 1 effective to induce an abortion.

9. The method of claim 8, wherein the composition is administered orally.

10. The method of claim 8, wherein 0.05–25 mg of the active compound is administered per kg. of body weight.

11. The method of claim 8, wherein 0.1–5 mg. of the active compound is administered per kg. of body weight.

12. The composition of claim 1 wherein the active compound is 1-$\beta$-heptanoyloxynorgestrel.